United States Patent [19]
Yokoi et al.

[11] Patent Number: 5,643,735
[45] Date of Patent: Jul. 1, 1997

[54] ANTI-THYMOSIN α1 MONOCLONAL ANTIBODY-PRODUCING HYBRIDOMA

[75] Inventors: Hiroyuki Yokoi; Takao Saito; Hideto Ohno, all of Ibaraki, Japan

[73] Assignee: Yuka Medias, Co., Ltd., Ibaraki, Japan

[21] Appl. No.: 412,564

[22] Filed: Mar. 29, 1995

[30] Foreign Application Priority Data

Sep. 9, 1994 [JP] Japan ................................. 6-215747

[51] Int. Cl.$^6$ ........................ G01N 33/53; G01N 33/542
[52] U.S. Cl. ........................ 435/7.9; 436/518; 436/540; 424/188.1; 514/12
[58] Field of Search ........................ 435/7.9; 424/188.1; 514/12; 436/518, 540

[56] References Cited

U.S. PATENT DOCUMENTS

| | | | |
|---|---|---|---|
| 4,079,127 | 3/1978 | Goldstein et al. | 514/12 |
| 4,264,571 | 4/1981 | Goldstein et al. | 436/540 |
| 4,339,427 | 7/1982 | Goldstein et al. | 436/540 |
| 4,427,783 | 1/1984 | Newman et al. | 436/542 |
| 4,950,590 | 8/1990 | Mutchnick et al. | 435/7.92 |
| 4,983,387 | 1/1991 | Goldstein et al. | 424/188.1 |
| 5,273,963 | 12/1993 | Moody | 514/12 |

FOREIGN PATENT DOCUMENTS 0 322 394   6/1989   European Pat. Off. .

OTHER PUBLICATIONS

1985 The Production, Characterization and Utilization of Monoclonal Antibodies to Thymosin Alpha–(1); Author: Oates, Karen, vol. 47/01–B Dissertation Abs Int.

Production and Characterization of a Monoclonal Antibody to Thymosin Alpha(1), Karen K Oates et al., George Washington Univ., Dept of Bio Journal—1984 Hybridoma V3, N1, p. 100.

*Alternative Immunoassays*, 1985, Chapter 6, Enzyme Immunoassays A. Volter and D.E. Bidwell, pp. 77–86.

*First Intern. Sympos. on Immunoenzymatic Techniques, INSERM Symposium #2*, 1976, B.K. Van Woeman and A.H. W.M. Schuurs, pp. 125–133.

*Enzyme Immunoassay*, CRC Press, 1980, Voller, A. Heterogeneous Enzyme–Immunoassays and Their Applications.

Sinopoli et al, "MicroELISA Detection of Thymosin α1 Released in Thymic Organ Cultures", *Journal of Immunological Methods*, 110 (1988) pp. 261–265.

Ishimura et al, "Antigenic Specificity of a Rabbit Antiserum Raised Against the 15–28 Segment of Thymosin α1," *Molecular Immunology*, vol. 23, No. 1, 1986, pp. 701–707.

Weller et al, "MicroELISA Method for Measurement of Human Serum Thymosin α1", *Journal of Immunological Methods*, 80 (1985), pp. 45–53.

Naylor et al, "Identification of Immunoreactive Forms of Tynmosin α1 in Serum and Supernatants by Combining HPCL and RIA," *Int. J. Immunopharmac.*, vol. 14, No. 7, 1992, pp. 1267–1278.

Incefy et al, "A Radioimmunoassay for Thymosin Alpha–1," *Journal of Immunological Methods*, 89 (1986), pp. 9–17.

Immunology Letters, vol. 16, No. 2, pp. 97–100, 1987, J. Ritter, et al., "Lack of Reactivity of Anti–Human Immunodeficiency Virus (HIV) P17/18 Antibodies Against α1 Thymosin and of Anti–α1 Thymosin Monoclonal Antibody Against P17/18 Protein".

Molecular Immunology, vol. 20, No. 10, pp. 1095–1097, 1983, C. Stahli, et al., "Monoclonal Antibodies to Thymosin α1".

Experientia, vol. 48, No. 4, pp. 398–402, 1992, O.E. Tsitsiloni, et al., "Evidence for the Extranuclear Localization of Thymosin in Thymus".

Journal of Immunological Methods, vol. 113, No. 2, pp. 175–184, 1988, O.E. Tsitsiloni, et al., "A Radioimmunoassay for Parathymosin α Using Antibodies to Synthetic N–Terminal Peptide 1–30".

Journal of Immunological Methods, vol. 106, No. 2, pp. 267–275, 1988, P.P. Yialouris, et al., "The Identification of Prothymosin α–Like Material in Vertebrate Lymphoid Organs by a Radioimmunoassay for the N–Terminal Decapeptide".

*Primary Examiner*—Marian C. Knode
*Assistant Examiner*—Ginny Allen Portner
*Attorney, Agent, or Firm*—Oblon, Spivak, McClelland, Maier & Neustadt, P.C.

[57] ABSTRACT

There are disclosed a hybridoma obtained by fusing a myeloma cell with an anti-thymosin α1 antibody-producing cell and selecting a hybridoma which produces a monoclonal antibody that recognizes the N-terminus of thymosin α1; an anti-thymosin α1 monoclonal antibody which is produced by the hybridoma, and a method for measuring thymosin α1 which comprises forming a three-component complex comprising thymosin α1, the anti-thymosin α1 monoclonal antibody (A), and an anti-thymosin α1 antibody (B) that recognizes a different site of thymosin α1 than antibody (A) does; forming a four-component complex of said three- component complex with a labeled substance (C) that specifically binds to antibody (A) or antibody (B) of the three-component complex; and detecting the labeled substance in said four-component complex.

13 Claims, 2 Drawing Sheets

# ANTI-THYMOSIN α1 MONOCLONAL ANTIBODY-PRODUCING HYBRIDOMA

BACKGROUND OF THE INVENTION

1. Field of the Invention

The present invention relates to a hybridoma which produces an anti-thymosin α1 monoclonal antibody, an antibody produced thereby, and a method for measurement of thymosin α1 by an immunological sandwich method using said antibody.

2. Discussion of the Background

Thymosin α1 is one of the thymus factors produced by thymus tissue. It is a polypeptide having a differentiation-inducing activity on T cells and plays an important role in maintenance of immunological functions. A polypeptide has been found in cattle that has the same amino acid sequence as that of human thymosin α1. Thymosin α1 consists of 28 amino acid residues and the first Ser [1] at the N-terminus is acetylated.

As a method for measuring thymosin α1, radioimmunoassays (RIA) which employ antisera have already been established (U.S. Pat. No. 4,264,571; U.S. Pat. No. 4,339,427; International Journal of Immunopharmacology 14, 1267–1278, 1992; Journal of Immunological Methods 110, 261–265, 1988; Molecular Immunology 23, 701–707, 1986; Journal of Immunological Methods 89, 9–17, 1986; and Journal of Immunological Methods 80, 45–53, 1985). Such immunoassays, which utilize a monoclonal antibody or a polyclonal antibody that recognize thymosin α1, have all been either competitive RIA or competitive enzyme immunoassays (EIA), using a labeled antigen. In these immunoassays, thymosin α1 which is labeled with a radioactive or non-radioactive labeling material does not exhibit exactly the same antigenecity to the anti-thymosin α1 antibody as the thymosin α1 present in a living body. In competitive immunoassays, not only thymosin α1 but a fragment of thymosin α1 or a peptide having a similar amino acid sequence also possibly participate so that high specificity for thymosin α1 has not been obtained. Also, the known immunoassays have not had satisfactory sensitivity.

The anti-thymosin α1 monoclonal antibodies and the anti-thymosin α1 polyclonal antibodies used in the above methods recognize only one part of thymosin α1. However, if one could obtain an antibody which specifically recognizes the N-terminus of thymosin α1, particularly the acetylated Ser [1] which is physiologically important, and another antibody which specifically recognizes the C-terminus of thymosin α1 then a sandwich immunoassay method would be available. The sandwich method is advantageous from the viewpoint of sensitivity and specificity as compared with the competition method.

SUMMARY OF THE INVENTION

An object of the present invention is to provide a hybridoma producing a monoclonal antibody which specifically recognizes the N-terminus of thymosin α1, an anti-thymosin α1 monoclonal antibody produced therefrom, and a method for measuring thymosin α1 using the same.

The present inventors have intensively studied so as to develop a monoclonal antibody which specifically recognizes the N-terminal fragment of thymosin α1 with a high affinity and obtained a hybridoma which produces a monoclonal antibody that recognizes the N-terminus of thymosin α1 containing the acetylated Ser [1]. This antibody provides a high sensitivity method for measuring thymosin α1.

The present invention relates to a hybridoma which is obtainable by fusing a myeloma cell with an anti-thymosin α1 antibody-producing cell; and selecting a hybridoma producing a monoclonal antibody which recognizes the N-terminus of thymosin α1 among the obtained hybridomas, an anti-thymosin α1 monoclonal antibody which is produced by the hybridoma, and a method for measuring thymosin α1 which comprises the steps of forming a three-component complex comprising thymosin α1, the anti-thymosin α1 monoclonal antibody (A) and an anti-thymosin α1 polyclonal antibody (B) which recognizes a different site of thymosin α1 than the monoclonal antibody does; forming a four component complex of the three component complex with a labeled substance (C) which specifically binds to the monoclonal antibody or the polyclonal antibody of the three component complex; and detecting the labeled substance in the four-component complex.

Figure 1:
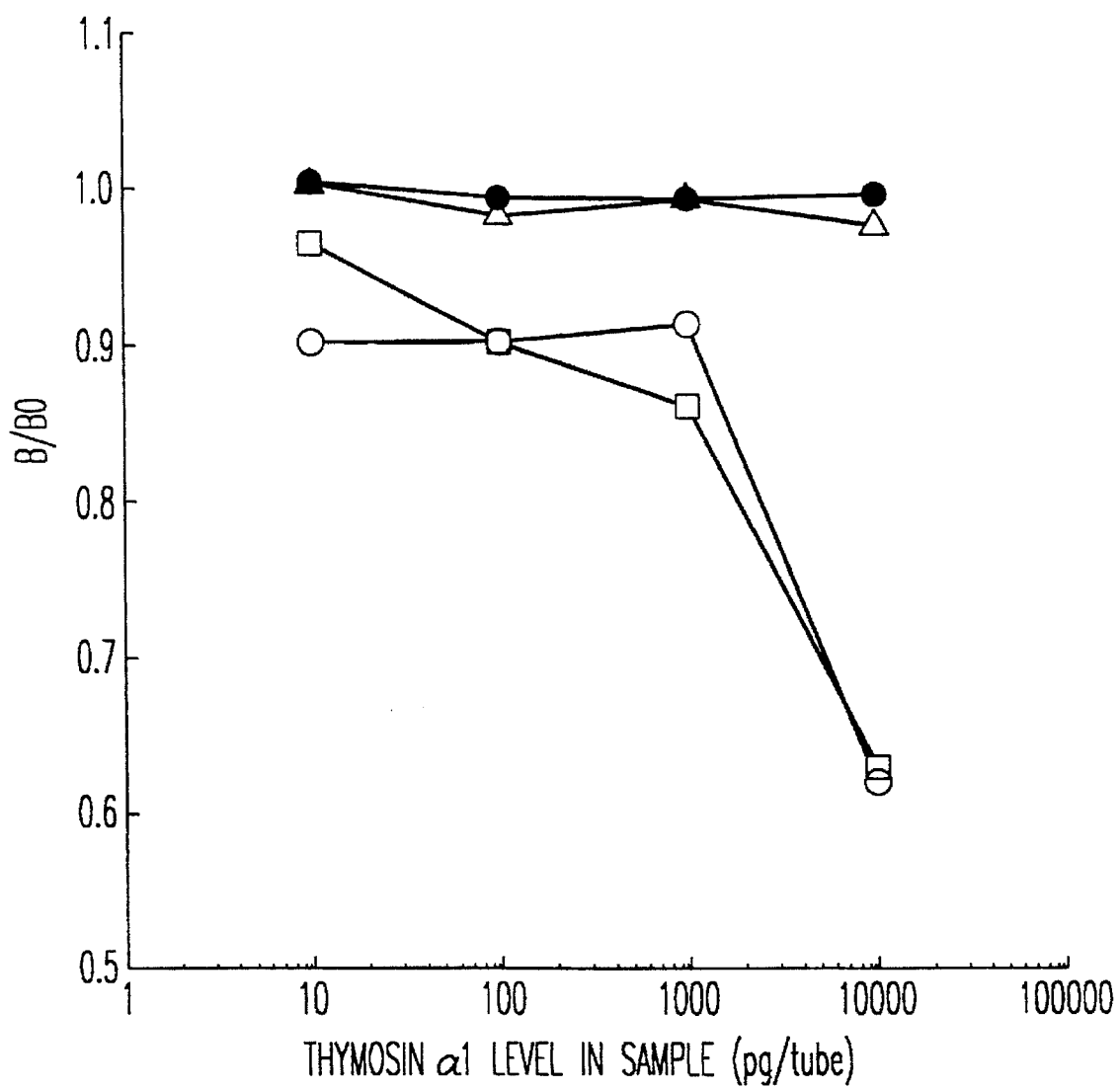
FIG. 1 is a graph showing the cross-reactivity of thymosin α1 [1-28] (○), desacetyl-thymosin α1 [1-28] (thymosin α1 [del-28]) (△), and a thymosin α1 fragment (thymosin α1 [1-15] (□), thymosin α1 [16-28] (●) with the monoclonal antibody MTH33G2 of the present invention.

DETAILED DESCRIPTION OF THE PREFERRED EMBODIMENT (1) Preparation of immunogen Thymosin α1 is a polypeptide consisting of 28 amino acid residues and known as a hapten with a low inducing ability for producing antibodies (immunogenicity) because of its relatively low molecular weight. Therefore, in order to use thymosin α1 or its fragment peptide as an antigen, it is linked with a carrier protein such as bovine serum albumin (BSA) and bovine thyroglobulin. Known methods for coupling a hapten to a carrier protein can be used including the glutaraldehyde cross-linking method, carbodiimide method, and homobifunctional cross-linking reagent method using 1,5-difluoro-2,4-dinitrobenzene [Marfey, S. P. and Tsai, K. H., Biochem. Biophys. Res. Commun. 65, 31 (1975)]. However, an overpolymerized polymer or an uneven hapten complex is easily formed so that such a hapten-carrier conjugate is not desirable as an immunogen in many cases. Particularly in thymosin α1, four Lys residues, three Asp residues and six Glu residues are present in the amino acid sequence. Therefore, not only intramolecular cross-linking or intermolecular cross-linking of thymosin α1 molecules, but also excessive cross-linking with the carrier protein are caused. The inventors prepared immunogens by using the glutaraldehyde method, the carbodiimide method and the homobifunctional cross-linking reagent method in order to prepare hapten complexes of thymosin α1 and BSA, and of thymosin α1 and bovine thyroglobulin. These preparations were used with an adjuvant to immunize a mouse or a rabbit. However, satisfactory antibody titer or satisfactory sensitivity could not be obtained.

Thus, the present inventors prepared a hapten-protein complex by a maleimide method using sulfosuccinimidyl 4-[N-maleimidomethyl]cyclohexane-1-carboxylate (Sulfo- SMCC) as a heterobifunctional cross-linking agent [Yoshitake, S. et al., J. Biochem. 92, 1413, (1982)] and found that if an animal is immunized with the complex, desirable effects can be obtained.

(2) Preparation of monoclonal antibody-producing hybridomas

The immunogen obtained by the maleimide method is emulsified in an appropriate adjuvant such as a complete Freund's adjuvant for immunization of mouse. The immunization is carried out by repeatedly inoculating the above emulsion into an intraperitoneum of a mouse with an interval of several weeks. Three days after the final inoculation, the spleen is isolated and used as an antibody-producing cell. At the same time, a myeloma cell strain having a suitable marker such as hypoxanthine-guanine-phosphoribosyl transferase deficiency (HGPRT$^-$) or thymidine kinase deficiency (TK$^-$) is prepared as a parent cell for obtaining a hybridoma by fusing the myeloma cell with the antibody-producing cell, and the myeloma cell is fused with the antibody-producing cell to have a hybridoma.

As a medium for obtaining the hybridoma, there may be used a conventional medium such as RPMI-1640 to which about 10% of calf serum (CS) is appropriately added. For example, myeloma cells as the parent cell and spleen cells are used in the ratio of about 4:10. As a fusing agent, 50% of polyethylene glycol (PEG) is preferably used because of high fusion ratio. The fused cells can be selected by a HAT selection method. Screening of the resulting hybridomas is carried out by known methods such as the RIA method, by using a culture supernatant so that a clone of a hybridoma which secrets the objective immunoglobulin can be selected. The screening may be carried out in two steps; a hybridoma which secrets an immunoglobulin which recognizes thymosin α1 [1-28] having acetylated Ser [1] is selected in the first step and then among the hybridomas selected in the first step, only a hybridoma which produces an immunoglobulin which does not recognize desacetyl-thymosin α1 [1-28] having non-acetylated Ser [1] at the N-terminus is selected in the second step.

In order to obtain single-cell clones of the hybridomas, for example, a microwell having 96 wells is inoculated with the hybridomas so that no more than one hybridoma is placed in each well and the growing clone is screened again. By repeating such subscreening procedures, single-cell clones are obtained. A hybridoma which was obtained in the Examples described below was named MTH33G2 and has been deposited at the NATIONAL INSTITUTE OF BIOSCIENCE AND HUMAN-TECHNOLOGY, Agency of Industrial Science and Technology, 1-3, Higashi 1-chome, Tsukuba-shi, Ibaraki-ken 305, Japan under FERM P-14461 (transferred to international deposition under BP-4971 on Jan. 17, 1995 under the Budapest Treaty).

(3) Preparation of monoclonal antibody

Then, in order to prepare the monoclonal antibody of the present invention, the hybridoma obtained above is cultured in a culture bottle (in vitro) or in intraperitoneum of mice (in vivo). If it is cultured in an in vitro system, the medium may be a conventional medium as described above to which CS is added. After cultivation in this medium for 3 to 5 days, the monoclonal antibody is obtained from the culture supernatant. In the in vivo culture, the hybridoma is inoculated into an intraperitoneum of a mouse and an ascites of the mouse is collected after 14 days, from which the monoclonal antibody can be obtained. The in vivo culture is preferred because a large amount of the antibody is efficiently produced as compared to the in vitro culture method.

The monoclonal antibody which is obtained from the thus obtained culture supernatant or ascites may be purified by appropriately combining known methods such as anion exchange column chromatography and protein A Sepharose column chromatography, as described in the Examples below.

The monoclonal antibody MTH33G2 produced by the hybridoma cell MTH33G2 of the present invention specifically recognizes thymosin α1 [1-28] having an acetylated Ser [1] at the N-terminus and does not react with desacetyl-thymosin α1 [1-28] having non-acetylated Ser [1] at the N-terminus or thymosin α1 [16-28] which is a half of thymosin α1 from the C-terminus, as shown in the Examples below. Therefore it is presumed that an epitope of thymosin α1 is located near the N-terminus of thymosin α1, in particular, a portion contained between the acetyl Ser [1] and Val [5] according to the epitope analysis.

(4) Rabbit anti-thymosin α1 [16-28] serum

Thymosin α1 [16-28]-bovine thyroglobulin complex is formed by the maleimide method from thymosin α1 [16-28] which is chemically synthesized by a known method. The obtained thymosin α1 [16-28]-bovine thyroglobulin complex is emulsified in a complete Freund's adjuvant and a rabbit is immunized with the obtained emulsion several times. Blood is collected from the rabbit 10 to 14 days after the final immunization to prepare a rabbit anti-thymosin α1 [16-28] serum. The rabbit anti-thymosin α1 serum obtained was named MCRO577.

The above polyclonal antibody is derived from a rabbit, but the source of the polyclonal antibody is not limited to a rabbit and the polyclonal antibody may be a specific antiserum obtained by immunizing an animal such as a horse, a goat or a chicken.

(5) Method for fixation of antibody to a solid phase

As a solid phase for fixing or immobilizing the antibody (A), there may be used a commercially available carrier for antigen-antibody reaction which is used for conventional immunoassays, for example particle-like substances made of glass or a synthetic resin (bead), a sphere-like substance (ball), a tube or a plate. To these carriers are adsorbed an antibody which recognizes the N-terminus or the C-terminus of thymosin α1. The adsorption step is carried out by allowing the carrier to stand, usually in a phosphate buffer at pH 6 to 10, preferably at around neutral pH, at room temperature overnight. The carrier to which the antibody has adsorbed is preserved in a phosphate buffer in the presence of sodium azide or at a cool place after drying.

(6) Preparation of a labeled substance (C)

As a labeled substance which recognizes the antibody (A) or (B) of the present invention, there may be mentioned a specific antibody to which a labeling substance is bound. The specific antibody is a specific anti-serum or an antibody obtained therefrom by purification, or a monoclonal antibody. It is obtained by immunizing, with an antibody of an animal from which the above monoclonal antibody or the above polyclonal antibody is obtained, another animal by using a known and commonly used method.

The labeling substance of the antibody may be either a non-radioactive substance or a radioactive substance. As the non-radioactive substance, there may be mentioned horseradish peroxidase (HRP), alkaline phosphatase and glucose oxidase. As the radioactive substance, there may be mentioned a radioisotope which emits radiation such as α rays, β rays and γ rays. A substance labeled with iodine 125 ($^{125}$I) is usually used in immunoassays. In Examples of the present invention, a $^{125}$I-labeled antibody labeled with sodium iodide (Na$^{125}$I) and chloramine T was used.

As for the combination of the antibodies for preparation of a reagent for immunoassay of thymosin α1, if the antibody (A) which recognizes the N-terminus of thymosin α1 is bound to a solid phase, a specific antibody to the antibody (B) which recognizes the C-terminus is used as the labeled antibody (C). If the antibody (A) which recognizes the C-terminus is bound to the solid phase, a specific antibody to the antibody (B) which recognizes the N-terminus is used as the labeled antibody (C). Generally speaking, since a relatively large amount of the antibody (A) is required for the solid phase, a monoclonal antibody which can be stably obtained in a large amount, for example, monoclonal antibody MTH33G2 of the present invention, is preferred for binding to the solid phase. The liquid phase antibody (B) may be either a monoclonal antibody or a polyclonal antibody provided it recognizes a site different from the site recognized by antibody (A) bound to the solid phase. For example, if monoclonal antibody MTH33G2 of the present invention is used as the antibody bound to the solid phase, the above anti-serum MCRO577 can be used as a liquid phase antibody. A monoclonal antibody which recognizes the C-terminus of thymosin α1 can be applied to the present invention as the antibody bound to the solid phase, while a monoclonal antibody or an anti-serum which recognizes the N-terminus can be applied to the present invention as the liquid phase antibody.

EXAMPLES

In the following, the present invention will be explained in detail by referring to Examples. However, these Examples should be regarded as an aid for concretely identifying the present invention and do not limit the scope of the present invention.

Preparation of Immunogen (1) Introduction of the maleimide group into thymosin α1 [1-28]

Synthesized thymosin α1 [1-28] in an amount of 5.3 mg was dissolved in 280 μl of 0.1M sodium phosphate buffer of pH 7.2, to which 5.9 mg of sulfosuccinimidyl-4-[N-maleimido-methyl]cyclohexane-1-carboxylate (Sulfo-SMCC; produced by Pierce Co.) was added and the mixture was stirred at 30° C. for 30 minutes. Then, the reaction mixture was passed through a Sephadex G-25 column (NAP-5 column; trade name, produced by Pharmacia Co.) equilibrated with 0.1M sodium phosphate buffer of pH 7.2 so as to remove excess reagent.

(2) Introduction of the thiol group into BSA (mercaptosuccinyl BSA)

BSA in an amount of 200 mg and 50 mg of S-acetylmercapto-succinic anhydride were incubated at 30° C. for 30 minutes in 5 ml of 0.1M sodium phosphate buffer of pH 7.0 while stirring sometimes. During these 30 minutes, the reaction mixture was kept at pH 7 by adding 1N NaOH solution. The reaction mixture was dialyzed with 0.1M sodium phosphate buffer having pH of 7.0 to remove unreacted reagent so that an acetylmercaptosuccinyl BSA was obtained.

The above obtained acetylmercaptosuccinyl BSA in an amount of 10 mg was dissolved in 0.2 ml of 0.1M sodium phosphate buffer of pH 7.2 containing 0.1M hydroxylamine and the mixture was allowed to react for 30 minutes for deacetylation and passed through a Sephadex G-25 column (NAP-5 column; trade name, produced by Pharmacia Co.) equilibrated with 0.1M sodium phosphate buffer of pH 6.0 containing 5 mM EDTA to remove excess reagent so that mercaptosuccinyl BSA was obtained [Kitagawa et al., "Immunological Experiment Procedure IX", edited by the Japanese Society of Immunology, page 3529 (1982)].

(3) Preparation of thymosin α1 [1-28]-BSA conjugate

Maleimidized thymosin α1 [1-28] obtained in (1) in an amount of 5.3 mg was added dropwise to 0.7 ml of 0.1M sodium phosphate buffer of pH 6.0 containing 4.5 mg of mercaptosuccinyl BSA obtained in (2) under stirring and the mixture was kept at a room temperature for 2 hours. The solution was dialyzed with 3 l of physiological saline five times for 24 hours. The dialyzed conjugate was stored at −20° C.

(4) Preparation of immunizer emulsion

To the above stored solution (containing 2 mg of thymosin α1 [1-28]-BSA conjugate) was added physiological saline up to 1 ml and the solution was emulsified in 1 ml of a complete Freund's adjuvant.

Producing Hybridoma

The above immunizer emulsion was intraperitoneally injected into a BALB/c female mouse (100 μl/mouse) and the mouse was additionally immunized after 2 weeks by the same method. The additional immunization was repeated every second week. After 10 weeks, the antibody titers from the test bleed were measured and to the caudal vein of one mouse which exhibited the most potent antigenecity, 100 μl of physiological saline containing thymosin α1 [1-28] was injected for the additional immunization (final boost). After 3 days, spleen cells of the mouse were collected for cell fusion.

The collected spleen cells ($1.0 \times 10^8$ cells) and myeloma cells P3x63AgSU.1 (ATCC CRL 1957) ($4 \times 10^7$ cells) were mixed in a RPMI-1640 medium (produced by Sigma Co.) and centrifuged at 1,150 rpm at 4° C. for 5 minutes. The obtained pellet was warmed up to 37° C., to which 1 ml of 50% PEG 4000 (PEG 1 g/RPMI-1640 1 ml) was added dropwise at 37° C. over 1 minute, followed by stirring for 1 minute. Then, 1 ml of RPMI-1640 (prewarmed at 37° C.) was added dropwise over 1 minute, followed by stirring for 1 minute. Then, 7 ml of RPMI-1640 (prewarmed at 37° C.) was added for dilution and the mixture was centrifugation-washed with 10% CS-added RPMI-1640 at 4° C.

The obtained cells were dispensed into 96 well tissue culture plates and cultured in a HAT medium (produced by Sigma Co.) for 2 weeks. A hybridoma was selected by a screening method described later and a cell in a well which exhibited the most potent antibody titer was cloned by a limiting dilution method. With this cloning, a clone which stably produces a large amount of antibody was selected and named MTH33G2. The MTH33G2 has been deposited at the NATIONAL INSTITUTE OF BIOSCIENCE AND HUMAN-TECHNOLOGY, Agency of Industrial Science and Technology under FERM BP-4971 under the Budapest Treaty as described above.

The antibody titer of an antiserum of the above immunized mouse or a supernatant of cultured hybridoma was assayed as described below. The anti-serum of the immunized mouse or the supernatant of the cultured hybridoma was obtained as a testing sample, and a reaction mixture containing 100 μl of the diluted sample, 100 μl of an assay buffer (0.1M sodium phosphate of pH 7.4, 0.15M NaCl, 1.0 mg/ml BSA, 0.5 mg/ml Tween 20 (trade name), and 0.2 mg/ml sodium azide) and 50 μl of $^{125}$I-[Tyr$^{29}$]-thymosin α1 [1-28] (10,000 cpm) was allowed to react at 4° C. for 24 hours. This mixture was mixed with 250 μl of the secondary antibody solution containing a rabbit anti-mouse IgG antibody, PEG6000 and Avicel and the mixture was allowed to react at 4° C. for 30 minutes. Then, the mixture was centrifuged at 4° C. at 3,000 rpm for 20 minutes and the radioactivity of the resulting precipitate was measured by a γ-counter (Aroca ARC-600, trade name) to determine the antibody titer of the diluted sample.

The above $^{125}$I-[Tyr$^{29}$]-thymosin α1 [1-28] was prepared by the chloramine T method. Namely, [Tyr$^{29}$]-thymosin α1 [1-28] in an amount of 4.8 μg and 0.5 mCi of Na$^{125}$I were mixed and to the mixture was added 3 μl of chloramine T (1.0 mg/ml), followed by addition of 25 μl of ascorbic acid (0.7 mg/ml) after 30 seconds. Further, 100 μl of 0.2 g/ml potassium iodide solution was added and the mixture was purified on ODS-120T reverse phase HPLC column (trade name, produced by TOSO Co.).

Preparation of Monoclonal Antibody

A BALB/c mouse which had been intraperitoneally injected with 0.5 ml of pristane 2 weeks before was intraperitoneally injected with the hybridoma MTH33G2 emulsified in RPMI-1640. Ascites was obtained and purified on a Protein A-Sepharose CL-4B column (trade name, produced by Pharmacia Co.) to have the monoclonal antibody MTH33G2.

Properties of Monoclonal Antibody MTH33G2

The isotype of the monoclonal antibody was identified by using a mouse monoclonal antibody subtyping kit (produced by BioRad Co.) and was identified as a subclass of IgG$_1$. The affinity was determined by a Scatchared plot and it was revealed that Ka is $4.0 \times 10^7 M^{-1}$.

The epitope was identified by examining the cross reactivity to various thymosin α1-related peptides by an RIA method. Namely, an ascites obtained from a mouse to which the hybridoma MTH33G2 had been injected was 1000 fold-diluted with an assay buffer (0.1M sodium phosphate of pH 7.4, 0.15M NaCl, 1.0 mg/ml BSA, 0.5 mg/ml Tween 20 and 0.2 mg/ml sodium azide). A mixture solution containing the diluted ascites in an amount of 100 μl, 100 μl of the standard thymosin α1 solution diluted with the assay buffer, and 50 μl of $^{125}$I-[Tyr$^{29}$]-thymosin α1 [1-28] (10,000 cpm) was allowed to react at 4° C. for 24 hours. The thus obtained mixture solution was mixed with 250 μl of the secondary antibody solution containing a rabbit anti-mouse IgG antibody, PEG6000 and Avicel and the mixture was allowed to react at 4° C. for 30 minutes. Then, the mixture was centrifuged at 4° C. at 3,000 rpm for 20 minutes and the radioactivity of the resulting precipitate was measured by a γ-counter (Aroca ARC-600, trade name).

For the preparation of the standard curve, a value was calculated by dividing the binding radioactivity in the presence of a known amount of thymosin μ1 by that in the absence of thymosin α1 (B/BO). The results are shown in FIG. 1. The epitope is thought to be contained in the residues 1 to 15 of thymosin α1 for the reason that the monoclonal antibody hardly reacted with desacetyl-thymosin α1 [1-28] in which the N-terminal is not acetylated, or the thymosin α1 [16-28] fragment. The monoclonal antibody recognized the acetyl group of the N-terminus of thymosin α1, and, to the contrary, did not recognize thymosin α1 in which the N-terminus was not acetylated.

Preparation of Polystyrene Balls Coated with the Monoclonal Anti-thymosin α1 Antibody Five hundred polystyrene balls having a diameter of 6.35 mm (produced by Immunochemical Co.) were placed in 150 ml of 0.05M potassium phosphate buffer of pH 7.2 and to this mixture was added 750 μg of the monoclonal anti-thymosin α1-IgG1 (monoclonal antibody MTH33G2). Then, the mixture was allowed to stand at room temperature overnight. The polystyrene balls were washed with a 0.05M potassium phosphate buffer of pH 7.2, dried and preserved in a refrigerator.

Preparation of Thymosin α1 [16-28]-bovine Thyroglobulin

[Cys]-thymosin α1 [16-28] obtained by adding Cys to the N-terminus of the thymosin α1 [16-28] peptide was coupled with a bovine thyroglobulin to which a maleimide group had been introduced.

The introduction of the maleimide group to the bovine thyroglobulin was performed as follows. Bovine thyroglobulin in an amount of 50 mg was dissolved in 5 ml of 0.1M sodium phosphate buffer of pH 7.0 and to the mixture was added 10 mg of sulfosuccinimidyl 4-[N-maleimidomethyl] cyclohexane-1-carboxylate (Sulfo-SMCC; produced by Pierce Co.), followed by stirring at 30° C. for 1 hour. Then, the reaction mixture was passed through a Sephadex G-25 column equilibrated with 0.1M sodium phosphate of pH 6.0 containing 5 mM EDTA to remove excess reagent.

To 7 ml of 0.1M sodium phosphate buffer of pH 6.0 containing 5 mM EDTA in which 50 mg of maleimide group-containing bovine thyroglobulin is dissolved, was added [Cys]-thymosin α1 [16-28], followed by stirring at 30° C. for 1 hour. The reaction solution was three times dialyzed with 15 l of physiological saline at 4° C., and stored at −20° C.

Immunization and Blood Sampling

The above thymosin α1 [16-28]-bovine thyroglobulin conjugate was emulsified in a complete Freund's adjuvant and was subcutaneously injected to 20 or more sites of the back of a rabbit. This procedure was repeated 10 times every second week and a blood sample was collected from a marginal ear vein of the rabbit IgG to have the anti-serum MCR0577.

Preparation of Anti-thymosin α1 Rabbit IgG

The anti-thymosin α1 serum (MCRO577) was purified by using an immunoaffinity column in which thymosin α1 [1-28] is bound to a Sepharose.

A thymosin α1 [1-28] Sepharose column was prepared as follows. At first, 1 g of an activated CH Sepharose 4B (trade name, produced by Pharmacia Co.) was allowed to react in 15 ml of ice cold 1 mM HCl for 15 minutes to cause the gel to swell. The swollen gel was immediately washed with 100 ml of 1 mM HCl. The washed gel was suspended in 4.5 ml of 0.1M sodium carbonate buffer of pH 8.0 containing 0.5M NaCl, to which 30 μg of thymosin α1 [1-28] was added, followed by mild stirring at room temperature for 2 hours. In order to wash out thymosin α1 [1-28] which was not bound to the gel, the gel was washed with 90 ml of 0.1M sodium carbonate buffer of pH 8.0 containing 0.5M NaCl. The gel was further washed with 15 ml of 0.1M sodium acetate of pH 4.0 containing 0.5M NaCl, followed by washing with 15 ml of 0.1M Tris hydrochloric acid of pH 8.0 containing 0.5M NaCl. The washed gel was preserved in a Dulbecco's PBS (phosphate buffer saline) containing sodium azide.

After the anti-thymosin α1 anti-serum (MCRO577) was passed through the above-prepared thymosin α1 [1-28] Sepharose column, the column was washed with a Dulbecco's PBS buffer so as to wash out any non-specific absorbed material remaining in the column. The elution from the column was carried out by using 0.2M glycine/hydrochloric acid buffer of pH 2.5 and the eluent was neutralized by adding 1M Tris hydrochloric acid of pH 8.0.

Preparation of Anti-rabbit IgG Goat Antibody Labeled with [$^{125}$I]

To 50 μl of 0.5M phosphate buffer containing 25 μg of anti-rabbit IgG goat IgG (produced by DAKO Co.) was added 1 mCi of Na$^{125}$I and also added 5 μl of chloramine T (2.0 mg/ml), followed by addition of 20 μl of ascorbic acid (2.0 mg/ml) after 5 minutes. Then, 20 μl of 0.2 g/ml potassium iodide solution was added and the mixture was purified with a Superose 12 column (trade name, produced by Pharmacia Co.).

Pretreatment of Plasma

A blood was sampled from a subject through the antecubital vein. The blood was sampled through an EDTA blood collection tube (produced by Terumo Co.) and plasma was separated therefrom by a centrifuge. The separated plasma was extracted with 25% acetonitrile by using a Sep-Pak C18 column (trade name, produced by Waters Co.).

Measurement of Thymosin α1 by a sandwich method (IRMA: Immunoradiometric Assay)

One polystyrene ball coated with the monoclonal anti-thymosin α1-IgG (monoclonal antibody MTH33G2), 5 ng of a rabbit anti-thymosin α1 antibody [16-28] and 50 μl of a 0.1M potassium phosphate buffer (pH 7.2; containing 1.0 mg/ml BSA, 1.0 mg/ml Tween 20 and 0.5 mg/ml sodium azide) were mixed and the mixture was added to the standard solution of thymosin α1 [1-28] or the extract of plasma with Sep-Pak C18 column (trade name, the total volume: 200 μl), followed by shaking at room temperature for 4 hours. The standard solution of thymosin α1 was diluted with a 0.1M potassium phosphate buffer (pH 7.2; containing 1.0 mg/ml BSA, 1.0 mg/ml Tween 20 and 0.5 mg/ml sodium azide) so that the final volume was 200 μl. Also, the plasma was extracted with Sep-Pak C18 column and the extract was dissolved in a 0.1M potassium phosphate buffer (pH 7.2; containing 1.0 mg/ml BSA, 1.0 mg/ml Tween 20 and 0.5 mg/ml sodium azide).

The solution portion of the reaction mixture was removed and the polystyrene ball was three times washed with 3 ml of distilled water. Then, the anti-rabbit IgG goat antibody labeled with [$^{125}$I] (200,000 cpm) and 200 μl of a 0.1M potassium phosphate buffer (pH 7.2; containing 20 mg/ml BSA, 0.5 mg/ml bovine-γ-globulin, 1.0 mg/ml Tween 20 and 0.5 mg/ml sodium azide) were added to the ball, mixed and allowed to stand at 4° C. for 18 hours. The solution portion of the mixture was removed and the polystyrene ball was three times washed as above described. Then, the radioactivity was measured by a γ-counter (Aroca ARC-600, trade name).

Specificity

Figure 2:
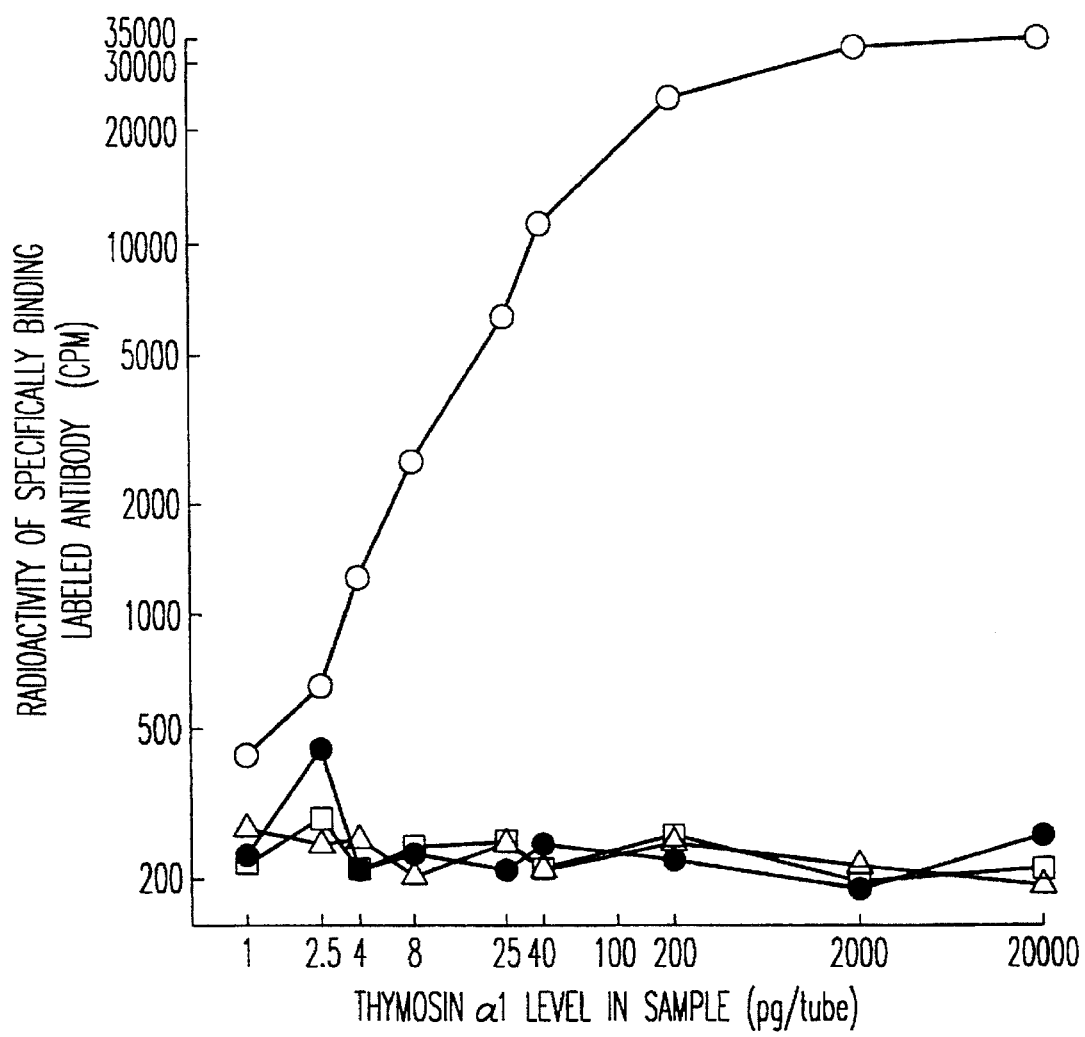
FIG. 2 is a graph showing a standard curve of thymosin α1 [1-28] by IRMA (○) and the cross-reactivity of desacetyl-thymosin α1 [1-28] [thymosin α1 (del-28) (△)], thymosin α1 fragment (thymosin α1 [1-15] (□)) and thymosin α1 [16-28] (●) with the monoclonal antibody MTH33G2 of the present invention.

The standard dilution curve of thymosin α1 obtained by a sandwich method using the above method is shown in FIG. 2. In this sandwich method which employs a monoclonal antibody which recognizes the N-terminus of thymosin α1 and a polyclonal antibody which recognizes the C-terminus of thymosin α1, the terminal thymosin α1 [1-15] fragment and the thymosin α1 [16-28] fragment were not detected. The desacetylthymosin α1 [1-28] in which the acetyl group at the N-terminus is missing was not detected either. These results correspond to the specificity of the antibody used. The mouse monoclonal IgG$_1$ (monoclonal antibody MTH33G2) which had been fixed to the polystyrene ball showed a specificity to the acetylated Ser [1]-containing N-terminus of thymosin α1, and the rabbit anti-thymosin α1-IgG showed a specificity to the thymosin α1 [16-28].

Sensitivity of Sandwich Method

Since the measurement lower limit of thymosin α1 is 1.0 pg per tube, when 200 μl of sample is used, the sensitivity for thymosin α1 should be 5.0 pg/ml (1.6 fm). This method has one order of magnitude higher sensitivity as compared with that of a conventional RIA (U.S. Pat. No. 4,339,427; International Journal of Immunopharmacology 14, 1267–1278, 1992; Journal of Immunological Methods 110, 261–265, 1988; Molecular Immunology 23, 701–707, 1986; Journal of Immunological Methods 89, 9–17, 1986; Journal of Immunological Methods 80, 45–53, 1985).

Plasma Thymosin α1 Level in a Healthy Man and a Patient with Thymoma

Plasma thymosin α1 levels in a healthy man and a patient with thymoma measured by the reagent of the present invention are shown in Table 1.

TABLE 1

| Sample No. | Measurement value (pg/ml) | Remarks |
| --- | --- | --- |
| 1 | 0.81 | Healthy man: plasma |
| 2 | 33.15 | Healthy neonatal: cord plasma |
| 3 | 9.26 | Patient with thymoma: plasma |
| 4 | 1.63 | Patient with thymoma: plasma |
| 5 | 6.61 | Patient with thymoma: plasma |
| 6 | 3.23 | Patient with thymoma: plasma |
| 7 | 3.83 | Patient with thymoma: plasma |

By using the reagent for immunoassay of thymosin α1 using the monoclonal antibody of the present invention, an intact thymosin α1 having acetylated Ser [1] at the N-terminus can be measured. With establishment of a method for measuring thymosin α1, a useful method for diagnosis of thymoma, immunodeficient diseases and autoimmune diseases is now available. Also, it has become possible to monitor thymosin α1 in drug therapy by monitoring the blood levels of thymosin α1.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A hybridoma, FERM BP-4971, obtained by fusing a myeloma cell with an anti-thymosin α1 antibody-producing cell; and selecting a hybridoma producing a monoclonal antibody which recognizes the N-terminus of thymosin α1 and does not recognize desacetyl-thymosin α1.

2. The hybridoma according to claim 1, wherein said monoclonal antibody recognizes an acetylated Ser at the N-terminus of thymosin α1.

3. The hybridoma according to claim 1, wherein the myeloma cell is a hypoxanthine-guanine-phosphoribosyl transferase-deficient or thymidine kinase-deficient cell.

4. The hybridoma according to claim 1, wherein the anti-thymosin α1 antibody-producing cell is obtained from the spleen of a mouse which has been immunized with thymosin α1 or thymosin α1 fragment peptide.

5. An anti-thymosin α1 monoclonal antibody which is produced by the hybridoma according to claim 1.

6. A method for measuring thymosin α1 which comprises the steps:

forming a three-component complex comprising thymosin α1, an anti-thymosin α1 monoclonal antibody (A), FERM BP-4971, which recognizes the N-terminus of thymosin α1 but which does not recognize desacetyl-thymosin α1, and an anti-thymosin α1 antibody (B) which recognizes a different site of thymosin α than said antibody (A) does;

forming a four-component complex of said three-component complex with a labeled substance (C) which specifically binds to the antibody (A) or the antibody (B) of said three-component complex; and detecting the labeled substance in said four-component complex.

7. The method for measuring thymosin α1 according to claim 6, wherein antibody (A) is a monoclonal antibody fixed to a solid phase.

8. The method of claim 6 wherein antibody (B) is a polyclonal antibody.

9. The method for measuring thymosin α1 according to claim 8, wherein the anti-thymosin α1 polyclonal antibody (B) is an anti-serum which is obtained from an animal immunized with thymosin α1 or thymosin α1 fragment peptide.

10. The method for measuring thymosin α1 according to claim 6, wherein the labeled substance (C) is a specific antibody which is bound to a labeling substance.

11. The method for measuring thymosin α1 according to claim 6, wherein the labeled substance (C) is labeled with a non-radioactive substance.

12. The method for measuring thymosin α1 according to claim 6, wherein the labeled substance (C) is labeled with a radioactive substance.

13. The method for measuring thymosin α1 according to claim 6, wherein said monoclonal antibody (A) is produced by a hybridoma obtained by fusing a myeloma cell with an anti-thymosin α1 antibody-producing cell, and selecting a hybridoma which produces a monoclonal antibody that recognizes the N-terminus of thymosin α1 and which does not recognize desacetyl-thymosin α1.

* * * * *